(12) United States Patent
Reina et al.

(10) Patent No.: US 7,896,546 B2
(45) Date of Patent: Mar. 1, 2011

(54) METHOD OF INCORPORATING AN X-RAY GRID INTO A CR CASSETTE

(75) Inventors: Leo Reina, Cary, IL (US); James Sorgani, Cary, IL (US)

(73) Assignee: Reina Imaging X-Ray Cassette Co., Inc., Crystal Lake, IL (US)

( * ) Notice: Subject to any disclaimer, the term of this patent is extended or adjusted under 35 U.S.C. 154(b) by 0 days.

(21) Appl. No.: 12/464,180

(22) Filed: May 12, 2009

(65) Prior Publication Data

US 2010/0290597 A1 Nov. 18, 2010

(51) Int. Cl.
*G03B 42/04* (2006.01)
(52) U.S. Cl. ......................................... 378/186
(58) Field of Classification Search .................. 378/154, 378/186, 189
See application file for complete search history.

(56) References Cited

U.S. PATENT DOCUMENTS

| | | | | |
|---|---|---|---|---|
| 4,380,087 A * | 4/1983 | Tanaka | ........................... | 378/186 |
| 4,429,412 A * | 1/1984 | Pierce et al. | ................... | 378/165 |
| 5,008,920 A * | 4/1991 | Gralak | ........................... | 378/185 |
| 5,276,333 A * | 1/1994 | Robertson | ...................... | 378/186 |
| 6,445,772 B1 * | 9/2002 | Campbell | ....................... | 378/154 |
| 7,329,890 B2 * | 2/2008 | Fletcher-Heath et al. | ..... | 250/581 |
| 7,556,426 B2 * | 7/2009 | Nakajo et al. | .................. | 378/188 |

* cited by examiner

*Primary Examiner* — Chih-Cheng G Kao
(74) *Attorney, Agent, or Firm* — Clifford Kraft

(57) ABSTRACT

A method of installing an x-ray grid into a CR cassette by opening the cassette, modifying parts of it, installing the grid and then re-closing the cassette with the grid inside. The preferred embodiment installs an x-ray grid into a Fuji 14×17 inch CR cassette by modifying parts that will interfere with the grid, removing a layer of protective material and placing the grid where the layer was, and then replacing the protective material by attaching it to the grid with adhesive.

15 Claims, 6 Drawing Sheets

METHOD OF INCORPORATING AN X-RAY GRID INTO A CR CASSETTE

BACKGROUND

1. Field of the Invention

The present invention relates generally to the field of x-ray cassettes and more particularly to a method for incorporating an x-ray grid into a CR (computed radiography) cassette.

2. Description of the Prior Art

X-ray grids are special filters that improve radiographic images. The grid generally contains metal or fiber filler strips that help prevent ghost and secondary images which produce unwanted noise in the image. A quality grid can reduce Moire patterns, grid aliasing and scanning lines, resulting in a better x-ray image.

Currently there are no manufacturers of grided Fuji, Agfa or Konica computed radiography cassettes, and currently no digital imaging manufacturers incorporate x-ray grids mounted into their CR cassettes 14×17 inches or smaller. External x-ray grids such as the Protect-a-Grid product manufactured by Reina Imaging Co. of Crystal Lake, Ill. have been used to fill this need. Since approximately 90% of x-rays taken are done on bedside as portable x-rays using a 14×17 inch cassette, there is a great need in the industry to incorporate an X-ray grid into a CR cassette.

The radiology community has been using X-ray Grid cassettes for the last 50 years they are widely accepted as the gold standard for bedside and specialized imaging such as trans lateral and decubitus imaging of the human anatomy Since the introduction of digital imaging to the radiology community approximately 15-18 years ago x-ray technologists have complained about the use of x-ray grids for bedside imaging due to the combined weight of a X-ray Grid plus Grid cover (typically used to protect the grid as well as forming a method of attachment of the x-ray grid to the cassette) added to the weight of the CR cassette. The combined weight can exceed 12-16 lbs. Another common complaint is the use of a grid cover plus the cassette as two separate bodies adds extra steps and unnecessary time to the x-ray procedure. Before digital imaging, the x-ray grid was commonly installed to the inside of the film cassette. The newer digital or CR cassettes, as they are called, have not allowed for this preference forcing the use of separate entities. It would be tremendously advantageous to be able to modify existing cassettes or manufacture a cassette with the grid inside.

SUMMARY OF THE INVENTION

The present invention relates to a method of installing an x-ray grid into a CR cassette, in particular Fuji, Agfa and Konica CR cassettes. An embodiment of the method presented uses a Fuji 14×17 inch CR Cassette as an example; however, it should be understood that the method of the present invention is applicable and can be used with many other CR cassettes. The method includes opening the cassette, modifying parts of it, installing the grid and then re-closing the cassette with the grid inside.

DESCRIPTION OF THE FIGURES

Several illustrations will now be presented to demonstrate graphically various features of the present invention. Attention is called to.

Several drawings and illustrations have been presented to aid in understanding the present invention. The scope of the present invention is not limited to what is shown in the figures.

DETAILED DESCRIPTION OF THE INVENTION

The present invention relates to a step-by-step method for adding an x-ray grid to a CR cassette. Generally the process includes opening the cassette, making room for the grid, installing the grid, preferably permanently, and closing up the cassette again.

The method can be performed with a minimum of standard tools. The embodiment of the method described herein can be performed with standard screw drivers, electric drill, countersink tool, allen wrench, small saw or plastic cutting tool and adhesive. Other tools, both hand and/or powered, may be used. Applying the method to different cassettes may require different sets of tools.

Figure 1A:
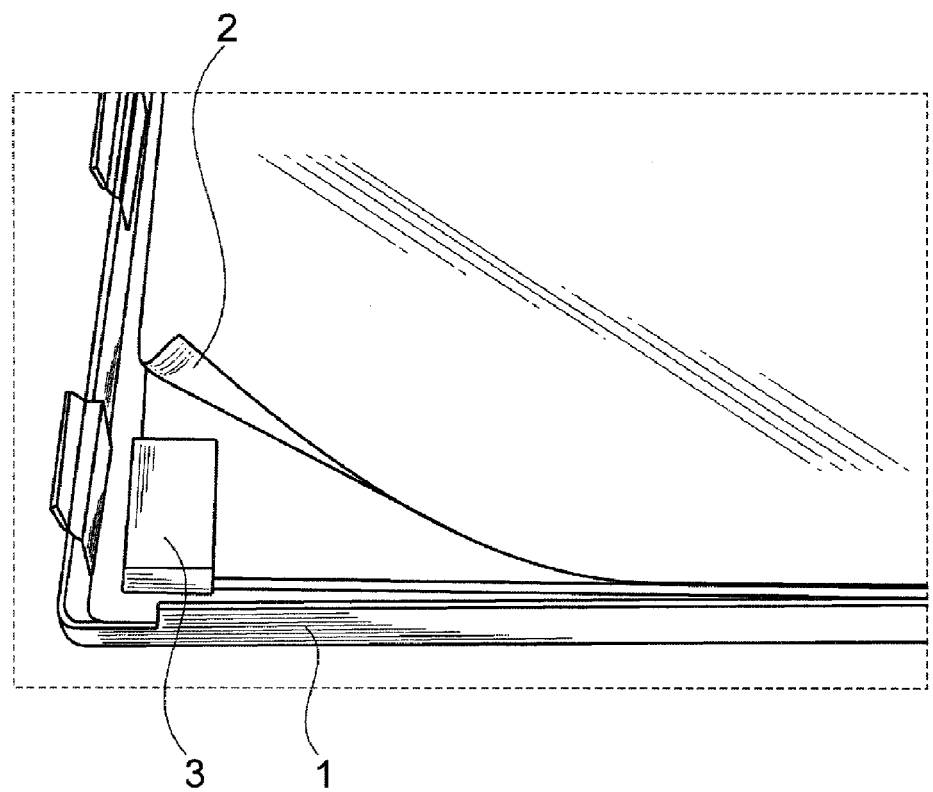
FIG. 1A shows an open Fuji cover and foam block.
Figure 1B:
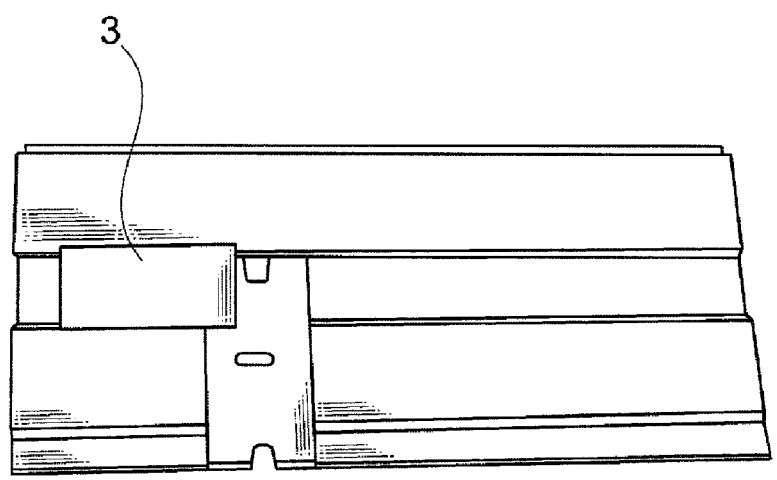
FIG. 1B shows the foam block of FIG. 1

The first step is to remove the cover from an existing cassette. The cover 1 of a Fuji 14×17 inch cassette is shown in FIG. 1A. Upon lifting up the protective layer 2, a foam block 3 can be seen This foam block 3 must be shaved down to around ½ its original thickness as shown in FIG. 1B.

Figure 2A:
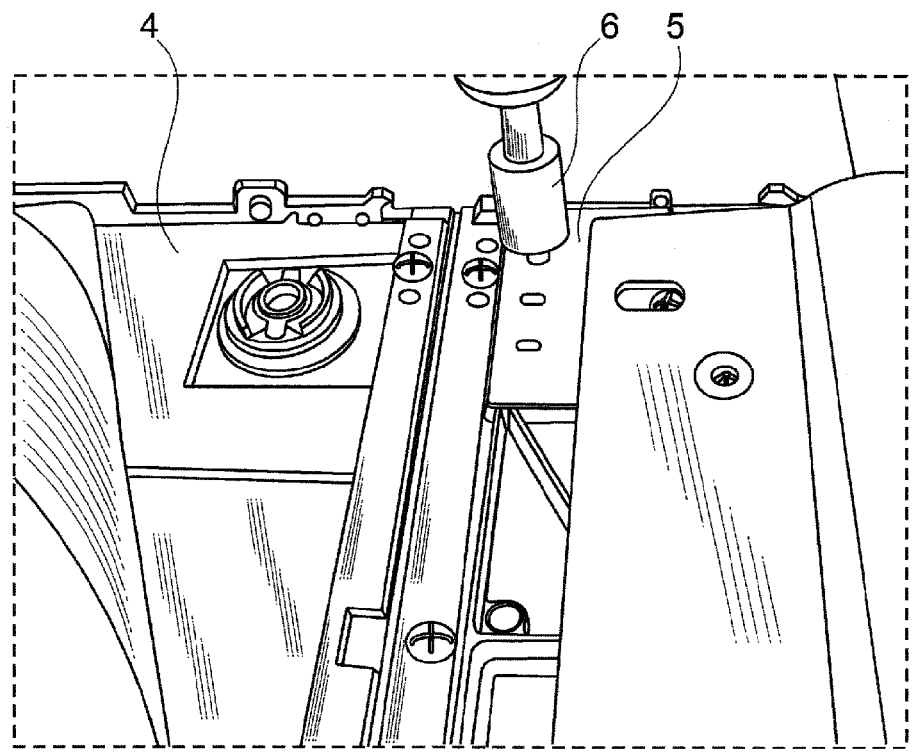
FIG. 2A shows a Fuji 14×17 CR cassette opened and the step of removing screws and countersinking.
Figure 2B:
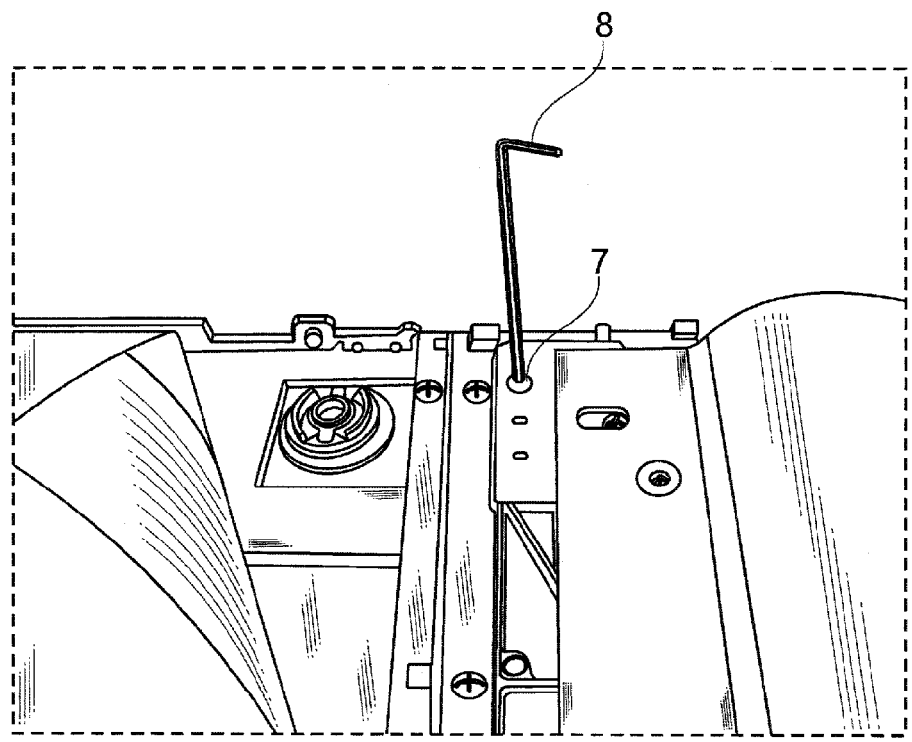
FIG. 2B shows the insertion of four new screws into the countersunk holes.

The next step is to remove four screws from each side of the cassette 4 as shown in FIG. 2A. The screws are located on metal tabs 5. After the screws are removed, the holes should be countersunk using a countersinking tool 5. The countersinking should be sufficient to accommodate four M2.5×0.43 thread 18-8 stainless steel flat head socket cap screws or similar screws. While these screws are preferred, any strong screws or bolts with flat heads can be used. Stainless steel is preferred because of its resistance to corrosion.

After all of the holes are countersunk, the screws should be inserted and tightened using an allen wrench or the appropriate tool for the particular screw chosen.

Figure 3A:
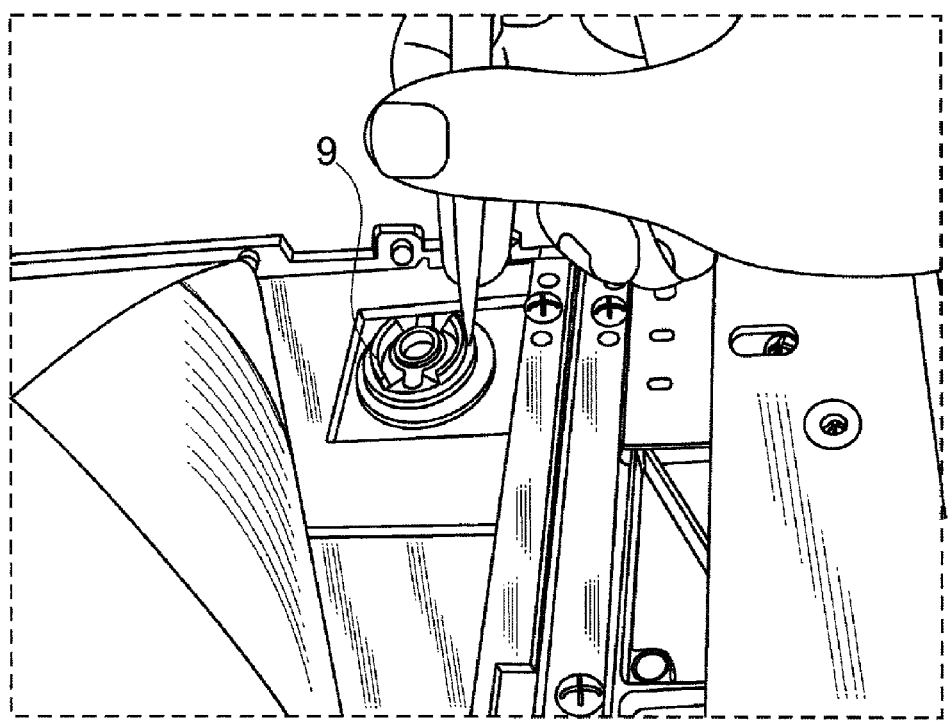
FIG. 3A shows an IP finger.
Figure 3B:
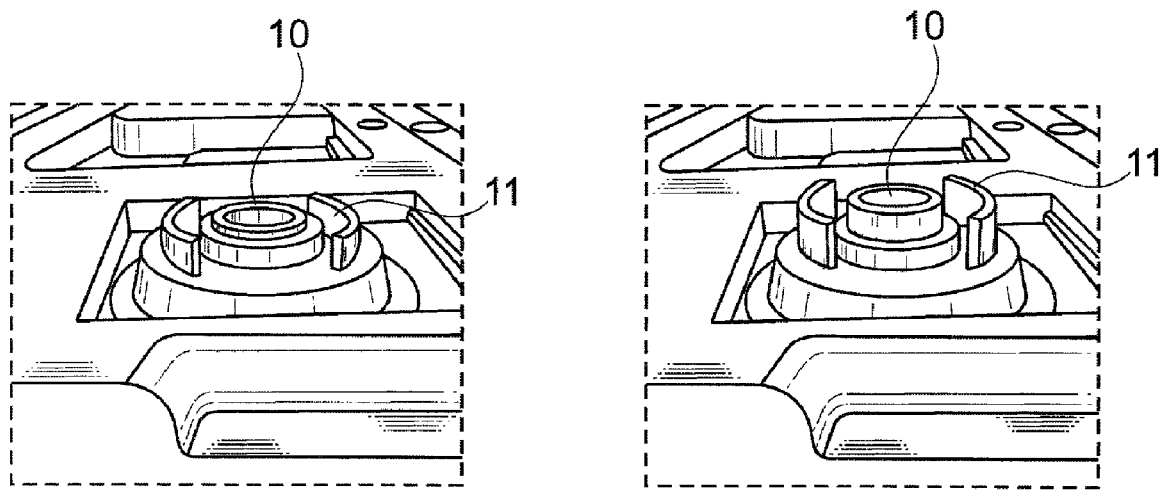
FIG. 3B IP (imaging plate) finger by removing material.

The next step is to remove both IP locking fingers 9 as shown in FIG. 3A. Each IP locking finger should have its height modified by removing material. FIG. 3B shows this process. The right hand figure shows the locking finger with an outer finger 10 and a center pole 11 before removal of the material, while the left hand figure shows the same parts after removal of the material. The outer finger 10 is originally around 3.6-3.8 mm high on the Fuji cassette. Approximately 2.0 mm of material should be removed to leave the outer finger around 1.6 mm. The center pole 11 is originally around 2.7 mm high. Approximately 1.6 mm of material should be removed to leave a height of the center pole 11 of around 1.1 mm. The Fuji locking fingers push down. Before the modification, the push-down is around 1.2-1.4 mm. After the modification, the push-down should be around 1.6-1.8 mm. After the locking fingers are modified, they should be re-installed.

Figure 4A:
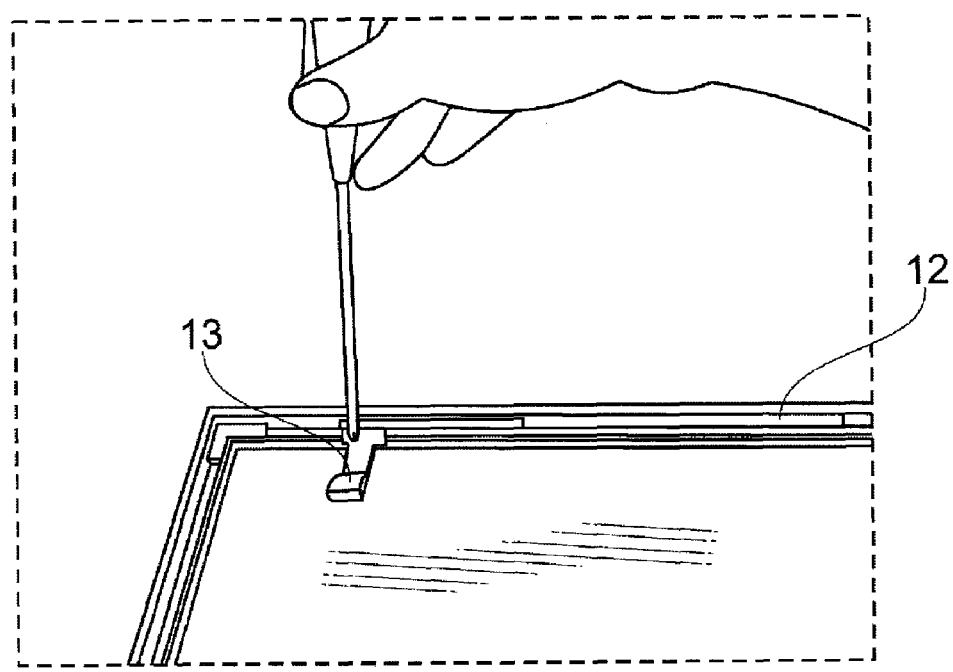
FIG. 4A shows removal of the IP holder.
Figure 4B:
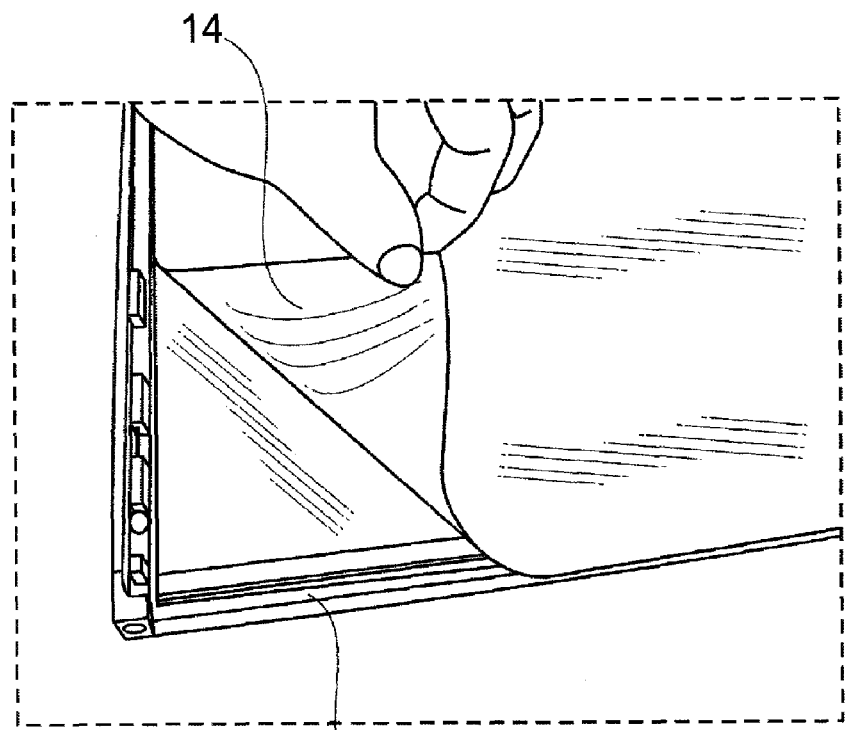
FIG. 4B shows removal of white material from the tube side.

The next step is to remove the IP holder 13 from the tube side of the cassette 12 as shown in FIG. 4A. Next, the white covering material 14 should also be removed from the tube side as shown in FIG. 4B.

Figure 5:
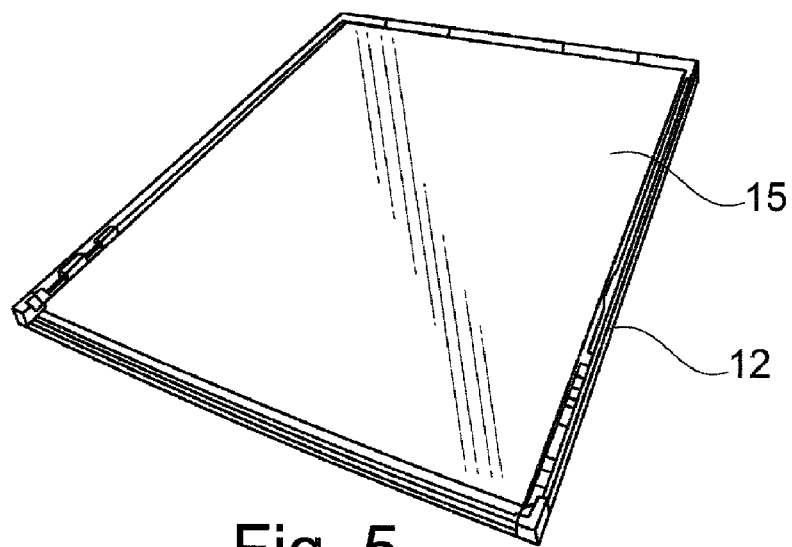
FIG. 5 shows laying the grid into the cassette where the white material was.

The next step is to lay the grid 15 (for example a 14×17 inch 8:1 ratio 178 LPI 40-72 inch focus grid) tube side down into the cassette shell 12 as shown in FIG. 5. The grid should be centered to the shell opening.

Figure 6:
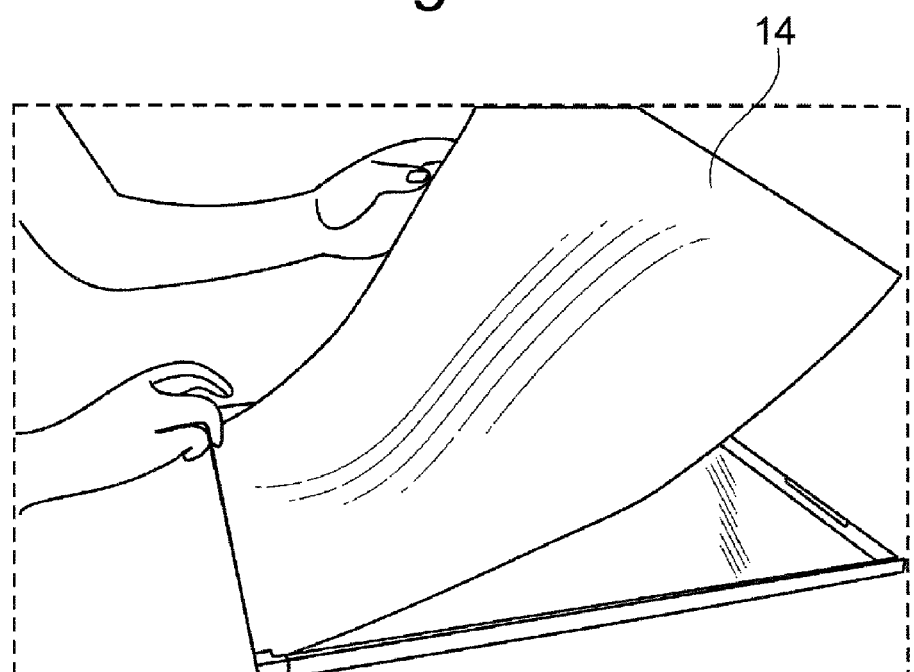
FIG. 6 shows re-installation of the white material over the grid.

The next step is to spray the white material with a glue or adhesive. A preferred adhesive is 3M 77 spray adhesive manufactured by 3M Corporation and known in the art. The white 14 material should then be re-installed over the grid as shown in FIG. 6.

Figure 7:
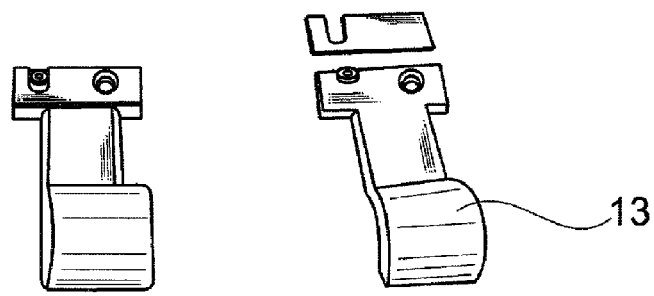
FIG. 7 shows shimming the IP hold-downs.
Figure 8:
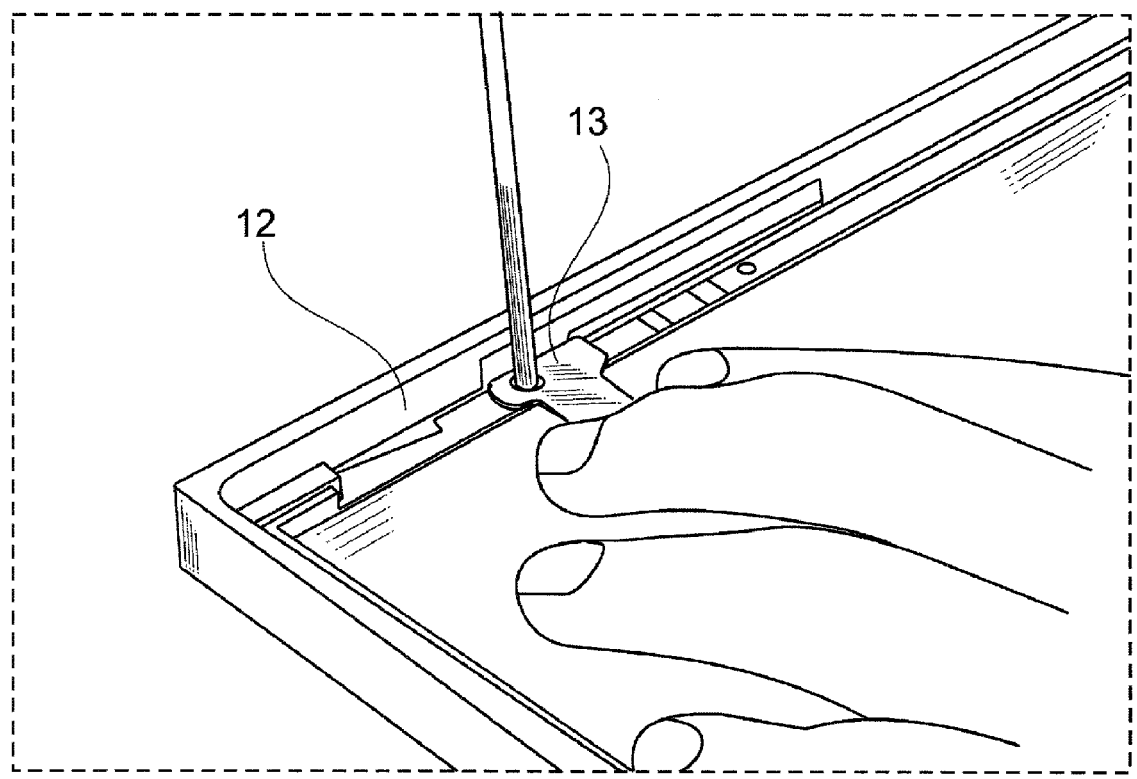
FIG. 8 shows installation of the shimmed IP hold-downs.

The IP hold downs 13 should be prepared with shims as shown in FIG. 7. A preferred shim is double stick tape known in the art. The screw hole in the IP holder should be countersunk, and then the IP holders with shims should be re-installed as shown in FIG. 8

The last step is the re-install the door of the cassette.

The result is a CR cassette that contains an x-ray grid ready for use.

Several descriptions and illustrations have been provided to aid in understanding the features of the present invention. One of skill in the art will realize that numerous changes and variations can be made without departing from the spirit of the invention. Each of these changes and variations is within the scope of the present invention.

We claim:

1. A method of installing an x-ray grid into a 14×17 inch CR (computed radiography) cassette comprising:
    opening said 14×17 inch CR cassette;
    replacing or modifying components that would interfere with installation of a grid into said cassette;
    installing a grid of proper size into said cassette;
    closing said cassette.

2. The method of claim 1 wherein the step of replacing or modifying components comprises removing material from IP (imaging plate) locking fingers.

3. The method of claim 1 wherein said step of replacing or modifying components comprises replacing regular screws with flat-head, countersunk screws.

4. The method of claim 1 the step of installing a grid of proper size comprises attaching said grid to said cassette with an adhesive.

5. The method of claim 1 wherein IP hold-downs are shimmed.

6. A method of modifying a Fuji 14×17 inch CR cassette having a front cover and tube side to contain an x-ray grid comprising:
    removing said front cover;
    modifying at least one foam block in said cover by making said at least one foam block thinner;
    replacing a plurality of regular screws in said cassette with countersunk, flat-head screws;
    modifying each IP locking finger by removing material from said each IP locking finger;
    removing all IP hold-downs;
    removing protective material from said tube side of said cassette;
    placing said grid where said protective material was;
    applying adhesive to said protective material;
    re-installing said protective material over said grid;
    re-installing said IP hold-downs, shimming if necessary;
    re-installing said front cover.

7. The method of claim 6 wherein said countersunk, flat-head screws are M2.5×0.43 thread, 18-8 stainless steel screws.

8. The method of claim 6 wherein said shimming is accomplished by using double-sided tape.

9. The method of claim 6 wherein said grid is a 14×17 inch, 8:1 ratio 178 LPI 40-72 inch focus grid.

10. The method of claim 6 wherein modifying said IP hold-downs is done by removing around 2 mm of material from an outer finger and around 1.6 mm of material from a center pole.

11. The method of claim 10 wherein push-down of said IP hold-downs after removal of said material is around 1.6-1.8 mm.

12. A method of modifying a 14×17 inch CR cassette having a front cover and tube side to contain an x-ray grid comprising:
    removing said front cover;
    modifying at least one foam block in said cover by making said at least one foam block thinner;
    replacing a plurality of regular screws in said cassette with countersunk, flat-head M2.5×0.43 thread, 18-8 stainless steel screws;
    modifying each IP locking finger by removing material from each IP locking finger;
    removing all IP hold-downs;
    removing protective material from said tube side of said cassette;
    placing a 14×17 inch, 8:1 ratio 178 LPI 40-72 inch focus grid where said protective material was;
    applying adhesive to said protective material;
    re-installing said protective material over said grid;
    re-installing said IP hold-downs, shimming if necessary;
    re-installing said front cover.

13. The method of claim 12 wherein said shimming is accomplished by using double-sided tape.

14. The method of claim 12 wherein modifying said IP hold-downs is done by removing around 2 mm of material from an outer finger and around 1.6 mm of material from a center pole.

15. The method of claim 14 wherein push-down of said IP hold-downs after removal of said material is around 1.6-1.8 mm.

* * * * *